United States Patent [19]

Noda et al.

[11] Patent Number: 5,137,733
[45] Date of Patent: Aug. 11, 1992

[54] CONTROLLED RELEASE PHARMACEUTICAL PREPARATION

[75] Inventors: Kazuo Noda, Takarazuka; Masao Kobayashi, Kyoto; Takashi Osawa, Toyonaka; Shigeyuki Ishikawa, Mino, all of Japan

[73] Assignee: Tanabe Seiyaku Co., Ltd., Osaka, Japan

[21] Appl. No.: 723,031

[22] Filed: Jun. 28, 1991

[30] Foreign Application Priority Data

Jun. 28, 1990 [JP] Japan .................. 2-171762

[51] Int. Cl.⁵ .......................... A61K 9/54; A61K 9/56; A61K 9/58
[52] U.S. Cl. .................................... 424/497; 424/490; 424/494; 424/495; 514/963
[58] Field of Search ................ 424/490, 494, 495, 497

[56] References Cited

U.S. PATENT DOCUMENTS

| | | | |
|---|---|---|---|
| 4,954,350 | 9/1990 | Jones et al. | 424/497 |
| 4,983,401 | 1/1991 | Eichel et al. | 424/497 |
| 5,002,776 | 3/1991 | Geoghegan et al. | 424/497 |
| 5,013,557 | 5/1991 | Tai | 424/493 |

FOREIGN PATENT DOCUMENTS

| | | |
|---|---|---|
| 315414 | 5/1989 | European Pat. Off. . |
| 386440 | 9/1990 | European Pat. Off. . |
| 59-44311 | 3/1984 | Japan . |
| 60-156617 | 8/1985 | Japan . |
| 60-193912 | 10/1985 | Japan . |

Primary Examiner—Thurman K. Page
Assistant Examiner—James Spear
Attorney, Agent, or Firm—Browdy and Neimark

[57] ABSTRACT

A controlled release pharmaceutical preparation comprising a core containing a medicinal compound and a coating layer containing a water-repellent salt and a water-insoluble and slightly water-permeable acrylic polymer having trimethylammoniumethyl group. Said preparation releases a medicinal compound in a sigmoid type dissolution pattern irrespective of the PH of a dissolution medium.

4 Claims, 4 Drawing Sheets o——o Plain granule containing diltiazem hydrochloride (control)

□——□ Controlled release pharmaceutical preparation (a)

+----+ Controlled release pharmaceutical preparation (b)

◇---◇ Controlled release pharmaceutical preparation (c)

△--△ Controlled release pharmaceutical preparation (d)

×--× Controlled release pharmaceutical preparation (e)

CONTROLLED RELEASE PHARMACEUTICAL PREPARATION

BACKGROUND OF THE INVENTION

The present invention relates to a controlled release pharmaceutical preparation, and more particularly to a so-called sigmoid type controlled release pharmaceutical preparation (Sigmoidal-Releasing System) from which a medicinal compound rapidly dissolves after a certain lag time.

Hitherto, concerning pharmaceutical preparations containing medicinal compounds, there have been various attempts to maintain their effects after the administration. For example, following two pharmaceutical preparations have been known. One is a sustained release pharmaceutical preparation (see Japanese Unexamined Patent Publication No. 156617/1985) in which a core is alternately coated with two compositions, namely, with a coating composition comprising a water-soluble polymer such as a polyvinyl alcohol or polyvinylpyrrolidone and a water-insoluble polymer such as ethylcellulose, polyvinyl chloride or Eudragit RS (trade mark, from Röhm Pharma, Germany), and a composition comprising diltiazem hydrochloride, an organic acid and a lubricant to form multi coating layers. And the other is a sustained release pharmaceutical preparation (see Japanese Unexamined Patent Publication No. 193913/1985) in which a core containing a medicinal active ingredient and an organic acid is spray-coated with an ethanol solution of an acrylic polymer having trimethylammoniumethyl group.

However, although these pharmaceutical preparations are suitable for releasing medicinal active ingredients gradually after the administration, they have a problem that the starting of the dissolution of their medicinal active ingredients can hardly be controlled.

On the other hand, it is known in the field of the pharmaceutical preparation that an increase in the thickness of the coating layer results in a delay of the starting of the dissolution of a medicinal active ingredient. However, it is also known that in this case the thick coat layer hinders rapid dissolution of a medicinal active ingredient after the starting of the dissolution and therefore an effective blood concentration can not be obtained rapidly.

An object of this invention is to provide a controlled release pharmaceutical preparation giving a so-called sigmoid type dissolution pattern wherein a lag time until the starting of the dissolution of a medicinal compound and the rate of the following dissolution can be controlled and the rate of the dissolution of the medicinal compound does not depend on the pH of a medium for the dissolution.

This and other objects of the present invention will become apparent from the description hereinafter.

SUMMARY OF THE INVENTION

It has been found that in case of coating a medicinal active ingredient with a water-insoluble and slightly water-permeable acrylic polymer having trimethylammoniumethyl group and a water-repellent salt such as magnecium stearate or calcium sterarate, ① the time until the starting of the dissolution of a medicinal active ingredient from the pharmaceutical preparation lengthens, ② the time until the starting of the dissolution can be controlled by the amount of the coating layer and ③ once the dissolution starts, almost 100% of the medicinal active ingredient dissolves irrespective of the amount of the coating layer.

The present invention provides a controlled release pharmaceutical preparation comprising a core containing a medicinal compound and a coating layer containing a water-repellent salt and a water-insoluble and slightly water-permeable acrylic polymer having trimethylammoniumethyl group.

DETAILED DESCRIPTION

Figure 1:
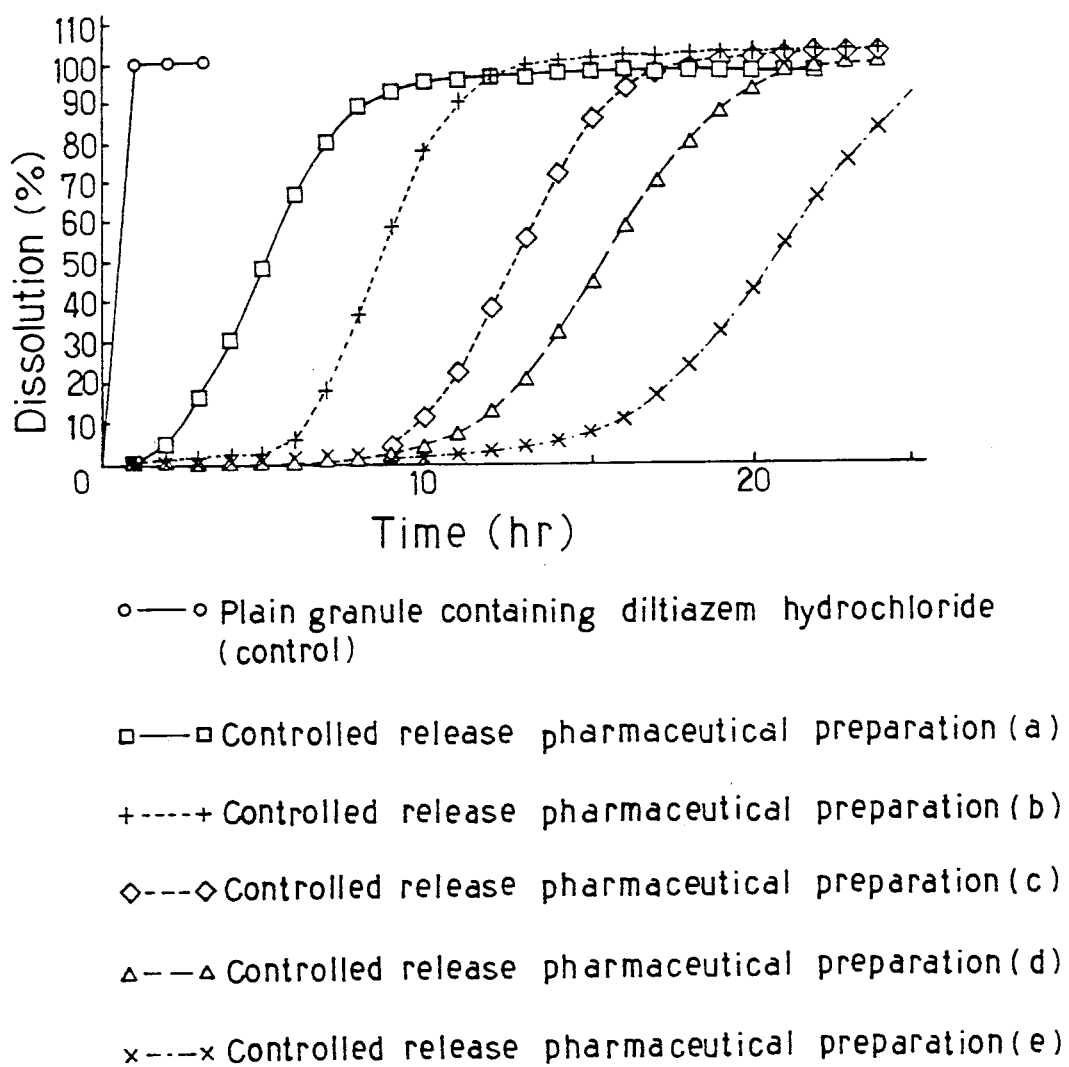
FIG. 1 is a graph showing the result of the dissolution test with water as to various controlled release granules (a) to (e) obtained in Test Example 1 which differ from each other in the amount of coating layer.

The controlled release pharmaceutical preparation of the present invention comprises a core containing a medicinal compound and a coating layer containing a water-repellent salt and a water-insoluble and slightly water-permeable acrylic polymer having trimethylammoniumethyl group, which surrounds said core. If desired, another coating layer of at least one material selected from the group consisting of ethylcellulose, hydroxypropylcellulose and a medicinal compound may be provided around said coating layer in the controlled release pharmaceutical preparation of the present invention.

In the present invention, a polymer of acrylic acid, methyl acrylate, ethyl acrylate, methacrylic acid, methyl methacrylate, ethyl methacrylate or the like, which has trimethylammoniumethyl group in the molecule, may be used as a water-insoluble and slightly water-permeable acrylic polymer constituting the coating layer. For instance, a copolymer of ethyl acrylate, methyl methacrylate and $\beta$-acryloyloxyethyltrimethylammonium chloride in which about 0.025 to about 0.033 mole of $\beta$-acryloyloxyethyltrimethylammonium chloride is contained per mole of the other neutral acrylic monomers is preferably used. Such copolymer is, for example, commercially available under trade mark "Eudragit RS" from Röhm Pharma, Germany or the like.

The above-mentioned polymer may contain, for instance, a small quantity of a water-permeable polymer. Such copolymer is, for example, commercially available under trade mark "Eudragit RL" from Röhm Pharma, Germany or the like.

As ethylcellulose or hydroxypropylcellulose which is a material of another coating layer provided around the coating layer of an acrylic polymer, for instance, ethylcellulose containing about 46.5 to about 51.0% of ethoxy group, hydroxypropylcellulose containing about 53.4 to about 77.5% of hydroxypropoxy group or the like can be suitably used.

As a water-repellent salt which constitute the coating layer with an acrylic polymer, a salt of higher fatty acid and an alkaline earth metal is preferably used. Concretely, examples of the salts are calcium stearate, magnesium stearate and the like.

In the present invention, as the ratio of the above-mentioned acrylic polymer and the water-repellent salt in the coating layer, it is adequate that about 0.5 to about 5 parts by weight, preferably about 1.5 to about 4.5 parts by weight and more preferably about 2 to about 4 parts by weight of the acrylic polymer is contained per part by weight of the water-repellent salt.

The amount of the coating layer for the core is variable a little depending on the form or the size of the core. However, it is preferable that the amount of the coating layer to be used tends to increase a bit depending on the increase of the surface area per unit weight, that is, the decrease of the particle size of the core. For example, in case of spherical particles having mean particle size of about 500 to about 1000 μm, the amount of the coating layer is about 5 to about 80%, preferably about 7 to about 50%, in particular, preferably about 8 to about 30%, based on the weight of the core.

In the present invention, the form of the core to be coated is not particularly limited and various forms such as plain tablet, pill, granule and fine granule may be suitably used. Above all, the granulated cores having means particle size of about 300 to about 5000 μm, in particular, about 500 to about 1500 μm may be preferably used.

The medicinal compound to be contained in the core is not particularly limited. For instance, calcium antagonists such as diltiazem hydrochloride, verapamil hydrochloride, nicardipine, nitrendipine and nimodipine, antiasthmatic agents such as theophylline and trimetaquinol, water soluble vitamins, antibiotics, antimalignantumor agents, antipyretic analgesics, antihyperglycemic agents and the like may be used.

In addition, various additives such as an excipient, a binder, a lubricant, an aggregation-preventing agent and a solubilizer for a medicinal compound which are usually used in this field may be contained in the core.

Examples of excipients are sugars such as sucrose, lactose, mannitol and glucose, starch, crystalline cellulose, calcium phosphate, calcium sulfate, calcium lactate and the like. Examples of carriers for regulating particle sizes are sucrose, lactose, starch, crystalline cellulose and the like. Examples of binders are polyvinylalcohol, polyacrylic acid, polymethacrylic acid, polyvinylpyrrolidone, glucose, sucrose, lactose, maltose, sorbitol, mannitol, hydroxyethylcellulose, hydroxypropylmethylcellulose, hydroxypropylcellulose, macrogols, arabic gum, gelatin, agar, starch and the like. Examples of lubricants are stearic acid, talc and the like. Examples of aggregation-preventing agents are the above-mentioned lubricants, silicone dioxide, colloidal silicone dioxide and the like. Examples of solubilizers for medicinal compounds are organic acids such as fumaric acid, succinic acid and malic acid and the like.

The pharmaceutical preparation of the present invention can be prepared by coating cores containing a medicinal compound with a dispersion of a water-insoluble and slightly water-permeable acrylic polymer having trimethylammoniumethyl group and a water-repellent salt. The preparation of the cores can be carried out according to the usual procedure for the preparation, for example, as described in Remingtons Pharmaceutical Sciences 17, 1603-1632, 1633-1643 (Mack Publishing Company, published in 1985). For Example, the cores can be prepared by granulating the composition of a medicinal compound, a binder and, as occasion demands, other additives such as an exicipent according to the method of wet oscillating granulation, rotating granulation, fluidizing bed granulation or the like to obtain granules. Alternatively, for example, the cores may be prepared using carriers for regulating particle sizes. That is, spherically granulated carriers may be coated with a medicinal compound according to the usual method such as powder coating method to obtain the cores. Powder coating can be carried out, for instance, by gradually adding a medicinal compound or a mixture of the medicinal compound and suitable additives such as an excipient with spraying a solution obtained by dissolving a binder in a suitable solvent such as water, a lower alcohol such as methanol, ethanol, propanol, isopropanol or butanol, a lower alkanone such as acetone or methylethylketone, chloroform, dichloromethane, dichloroethane or a mixture thereof, on carrier particles to be cores, according to the method of rotating granulation, pan coating, fluidizing bed coating or the like.

The coating for thus obtained cores can be carried out by adhering a dispersion of a water-repellent salt and an acrylic polymer to the cores followed by drying.

As a dispersion medium for the above-mentioned component of the coating layer, water, an alcohol such as methanol, ethanol or propanol, a ketone such as acetone, a halogenated hydrocarbon such as methylenechloride or chloroform, a mixture thereof or the like is exemplified. Water, an alcohol or a mixture thereof is preferable, and ethanol or a mixture of ethanol and water is particularly preferable.

The coating can be carried out according to a method generally used in the art for preparation such as the method of fluidizing bed coating or pan coating. For example, in case of the method of fluidizing bed coating, the coating can be carried out as follows. That is, while the cores are fluidized in an apparatus by means of air pressure, they are spray-coated with an aqueous dispersion of a water-repellent salt and an acrylic acid polymer at an adequate rate from the nozzle of the spray-gun.

The concentration of a water-repellent salt and an acrylic polymer in the dispersion is not particularly limited, but it is preferable that these components are added within the above-mentioned scope of the preferable proportion of both components, to be the concentration of about 5 to about 40% by weight. In addition, a plasticizer, a coloring agent and the like may be contained in the dispersion. As a plasticizer, for instance, triacetin, triethyl citrate, acetyltributyl citrate, diethyl phthalate, polyethyleneglycol, polysorbate or the like can be suitably used. The amount of the plasticizer to be used is preferably about 5 to about 40% by weight based on the weight of an acrylic polymer.

The drying of thus obtained coating layer can be easily carried out, for example, by heating at about 35° to about 100° C., particularly about 40° to about 70° C.

The other form of the pharmaceutical preparation of the present invention wherein another coating layer made of at least one material selected from the group consisting of ethylcellulose, hydroxypropylcellulose and a medicinal compound is provided around the coating layer containing a water-repellent salt and a water-insoluble and slightly water-permeable acrylic polymer having trimethylammoniumethyl group, can be easily prepared by further coating the above-mentioned pharmaceutical preparation having the coating layer of an acrylic polymer with these components according to the usual method.

For example, in case of coating with ethylcellulose or hydroxypropylcellulose, the solution prepared by dissolving ethylcellulose or hydroxypropylcellulose in water, methanol, ethanol, acetone or a mixed solvent thereof to be the concentration of about 0.5 to about 10%, may be sprayed for coating. In case of coating with a medicinal compound, the solution or dispersion containing said medicinal compound or a mixture of the medicinal compound and suitable additives such as an excipient and a binder may be sprayed for coating according to the usual method. As the additives, for instance, the above-mentioned binders and excipients may be suitably used.

Thus obtained controlled release pharmaceutical preparation of the present invention may be administered as it is or in a form filled in capsules.

The pharmaceutical preparation of the present invention has the following characteristics because of its coating layer of a slightly water-permeable acrylic polymer. That is, a medicinal active ingredient rapidly dissolves from the preparation after a certain period which depends upon the amount of the coating layer although it never dissolves after administration until the certain time passes. Besides, the time until the start of the dissolution of a medicinal active ingredient is optionally adjustable by changing the amount of the coating layer.

Therefore, the pharmaceutical preparation of the present invention is useful as a pharmaceutical preparation wherein the starting of the dissolution of a pharmaceutical compound can be adjusted by itself. And it is further useful that the pharmaceutical preparation which can retain an effective blood concentration for many hours can be obtained by combining various pharmaceutical preparations which differ from each other in the amount of the coating layer or in a kind of a component of the coating layer, according to the present invention.

The pharmaceutical preparation of the present invention wherein the coating layer of a slightly water-permeable acrylic polymer is further coated with ethylcellulose, hydroxypropylcellulose or the like, has a following advantage. That is, because the dissolution rate of a medicinal compound after a lag time in such pharmaceutical preparation is smaller than that in a pharmaceutical preparation whose coating layer of an acrylic polymer and a water-repellent salt is not further coated, the most suitable dissolution pattern can be obtained by employing the above-mentioned coating layer in accordance with a kind of medicinal active ingredient. In addition, these pharmaceutical preparations also have an advantage of being useful for preventing the aggregation of the preparations, which occurs during preparing them.

Further the pharmaceutical preparation wherein the layer of a medicinal compound is provided around the coating layer of an acrylic polymer can start the dissolution of the inside medicinal compound when the blood concentration originated in the outside medicinal compound has lowered after its dissolution followed by the rise of its concentration, by adjusting the amounts of the medicinal compound layer and an acrylic polymer layer or providing an another coating layer of hydroxypropylcellulose or the like around the layer of a medicinal compound. Therefore, the pharmaceutical preparation of the present invention has an advantage that it can be administered as a pharmaceutical preparation suitable for once administration a day.

The present invention is more specifically described and explained by means of the following Test Examples and Examples in which all percents and parts are by weight unless otherwise noted. It is to be understood that the present invention is not limited to the Examples, and various changes and modifications may be made in the invention without departing from the spirit and scope thereof.

TEST EXAMPLE 1

(1) Preparation

Nonpareil (granulated sucrose, from Freund Industrial Co. Ltd., Japan) having the diameter of 350 to 500 $\mu$m (80 g) was put into the centrifugal fluidizing type granulating and coating apparatus (CF-360EX Type, made by Freund Industrial Co. Ltd., Japan) and rolled in it.

Thereto was gradually added fine powder of diltiazem hydrochloride (900 g) with spraying a solution of polyvinylpyrrolidone (20 g) dissolved in a mixture of water and ethanol (3:2) (640 g). Nonpareil was thus coated around its surface with diltiazem hydrochloride to obtain plain granule containing diltiazem hydrochloride in the amount of 90%.

Then this plain granule was spray-coated with a solution containing 30 parts of Eudragit RS, 10 parts of calcium stearate and 3 parts of triethyl citrate to obtain various controlled release pharmaceutical preparations (a) to (e) containing diltiazem hydrochloride, which differ from each other in the amount of the coating layer on the plain granule as shown in Table 1.

TABLE 1

| Controlled release pharmaceutical preparation | Amount of coating layer* |
| --- | --- |
| (a) | 12 |
| (b) | 14 |
| (c) | 16 |
| (d) | 20 |
| (e) | 22 |

*Amount of coating layer (g) per 100 g of plain granule

(2) Comparison of Dissolution Patterns

① The dissolution test according to the paddle method (37° C., water, 100 rpm) based on the specification of the dissolution test under 11th revised Japanese Pharmacopoeia (JPXI) was carried out with respect to each pharmaceutical preparation obtained in the above.

Plain granule containing diltiazem hydrochloride which was not yet coated was used as a control preparation.

② The dissolution test according to the same condition as in ① was carried out with respect to the pharmaceutical preparation (d) in Table 1, with first fluid (JPXI), second fluid (JPXI) and water.

(3) Result

The result of the dissolution test in ① is shown in FIG. 1. It is recognized that according to the pharmaceutical preparation of the present invention, the medicinal compounds are completely released and their dissolution patterns shows sigmoid type in water, although the lag time until the start of the dissolution is prolonged according as the increase of the amount of the coating layer in the pharmaceutical preparation.

Figure 2:
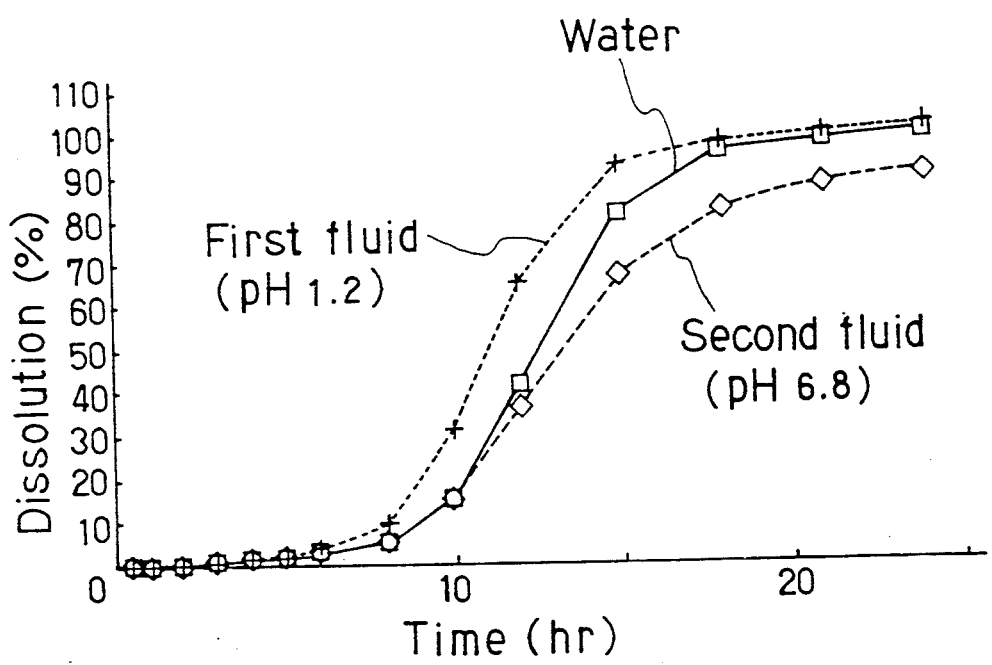
FIG. 2 is a graph showing the result of the dissolution test with water, first fluid and second fluid as to the controlled release granule (d) obtained in Test Example 1.

The result of the dissolution test in (2) is shown in FIG. 2. It is shown that the pharmaceutical preparation of the present invention shows the same dissolution patterns both with first fluid and second fluid as that with water. This result shows that the pharmaceutical preparation of the present invention has the pH-independent dissolution property. Therefore, it is recognized that according to the pharmaceutical preparation of the present invention, a medicinal compound dissolves immediately after a lag time irrespective of the pH change in the digestive tract.

TEST EXAMPLE 2

The controlled release pharmaceutical preparation (d) obtained in Test Example 1 was orally administered (dose: 100 mg as the amount of diltiazem hydrochloride) to dogs. After administration, the blood was collected from vein at fixed times. The plasma concentration of diltiazem hydrochloride was measured by high performance liquid chromatography.

Figure 3:
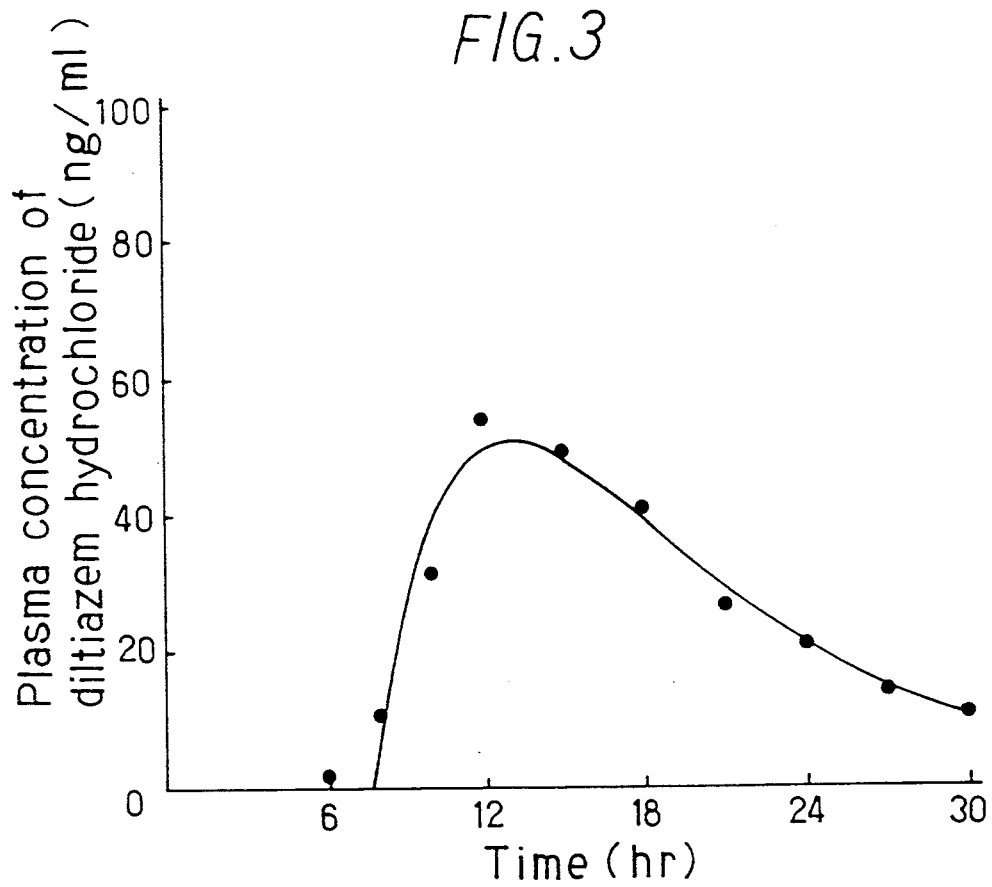
FIG. 3 is a graph showing the change in blood concentration of a medicinal compound in case that the granule (d) was administered to dogs in Test Example 2.

The result is shown in FIG. 3. It is recognized that the plasma concentration level is still high 30 hours later after the lag time of 8 hours.

TEST EXAMPLE 3

The controlled release pharmaceutical preparations (a) (373 g) and (d) (800 g) obtained in the Test Example 1 and the plain granule (111 g) containing diltiazem hydrochloride were mixed. The mixture (128 mg) containing 100 mg of diltiazem hydrochloride was filled into a gelatin capsule to obtain a controlled release capsule.

Then the dissolution test according to the paddle method (37° C., water, 100 rpm) under JPXI was carried out in the same manner as in Test Example 1 with respect to the controlled release capsule obtained in the above.

Figure 4:
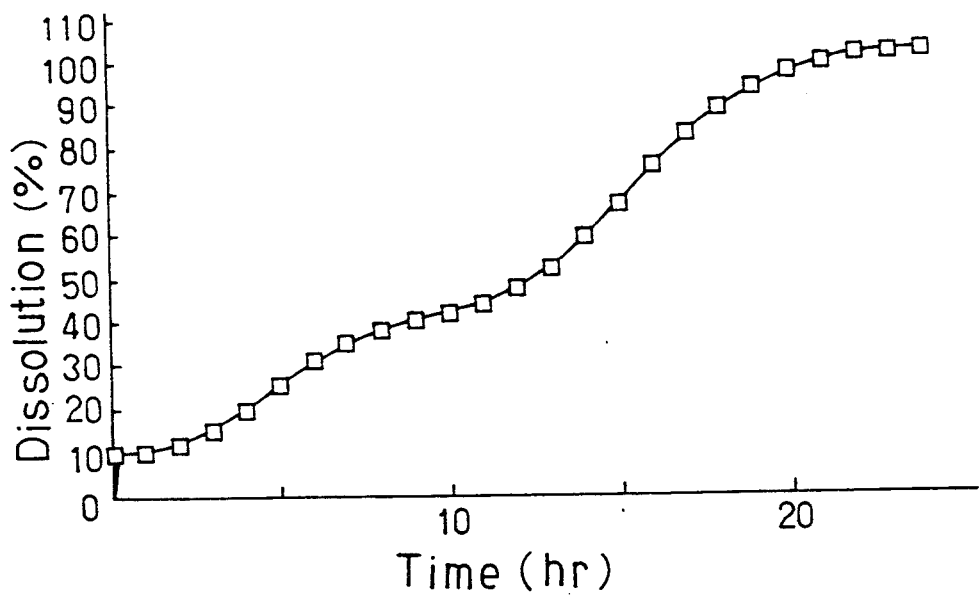
FIG. 4 is a graph showing the result of the dissolution test as to a capsule containing various controlled release granules obtained in Test Example 3 which differ from each other in the amount of the coating layer.

The result of the dissolution test shows the durative dissolution pattern for 24 hours as shown in FIG. 4. Therefore, it is clear that a preparation can be designed to release a drug continuously for long hours by combining various pharmaceutical preparations of the present invention.

EXAMPLE 1

Nonpareil 103 (granulated sucrose, from Freund Industrial Co. Ltd., Japan) which was a spherically granulated sucrose having the diameter of 350 to 500 μm (800 g) was put into the centrifugal fluidizing type granulating and coating apparatus (made by Freund Industrial Co. Ltd., Japan hereinafter referred to as CF apparatus) and rolled in it. Thereto was gradually spread fine powder of diltiazem hydrochloride (9 kg) with spraying a solution of polyvinylpyrrolidone (200 g) in a mixture of ethanol and water (2:3) (6.4 kg). Plain granule having the diameter of 12 to 20 mesh (1400 to 840 μm) containing diltiazem hydrochloride, wherein Nonpareil was coated around its surface with diltiazem hydrochloride, was thus prepared. Then the obtained plain granule (1 kg) containing diltiazem hydrochloride was put into CF apparatus and spray-coated with a solution consisting of Eudragit RS (a copolymer of ethyl acrylate, methyl methacrylate and β-acryloyloxyethyltrimethylammonium chloride, from Röhm Pharma, Germany) (84 g), calcium stearate (28 g), triethyl citrate (8 g), ethanol (160 g) and water (320 g). After coating, the granule was dried by heating at 60° C. for 16 hours to obtain a controlled release pharmaceutical preparation containing diltiazem hydrochloride (yield: 1.12 kg).

EXAMPLE 2

The procedure was carried out in the same manner as in Example 1 except that a mixture of Eudragit RS (112 g), calcium stearate (37 g), triethyl citrate (11 g), ethanol (210 g) and water (430 g) was used as a coating solution to obtain a controlled release pharmaceutical preparation containing diltiazem hydrochloride (yield: 1.16 kg).

EXAMPLE 3

The procedure was carried out in the same manner as in Example 1 except that a mixture of Eudragit RS (140 g), calcium stearate (47 g), triethyl citrate (14 g), ethanol (267 g) and water (533 g) was used as a coating solution to obtain a controlled release pharmaceutical preparation containing diltiazem hydrochloride (yield: 1.2 kg).

EXAMPLE 4

The procedure was carried out in the same manner as in Example 3 except that magnesium stearate (47 g) was used instead of calcium stearate to obtain a controlled release pharmaceutical preparation containing diltiazem hydrochloride (yield: 1.2 kg).

EXAMPLE 5

The procedure was carried out in the same manner as in Example 3 except that tributyl acetylcitrate (14 g) was used instead of triethyl citrate as a plasticizer to obtain a controlled release pharmaceutical preparation containing diltiazem hydrochloride (yield: 1.2 kg).

EXAMPLE 6

The procedure was carried out in the same manner as in Example 3 except that both Eudragit RS (126 g) and Eudragit RL (14 g) were used instead of Eudragit RS (140 g) to obtain a controlled release pharmaceutical preparation containing diltiazem hydrochloride (yield: 1.2 kg).

EXAMPLE 7

The controlled release pharmaceutical preparation (0.56 kg) containing diltiazem hydrochloride obtained in the same manner as in Example 3 was put into CF apparatus and spray-coated with a coating solution consisting of ethylcellulose (9.5 g), hydroxypropylcellulose (0.5 g), ethanol (59 g) and water (32 g). Then the preparation was dried at 60° C. for 16 hours to obtain a controlled release pharmaceutical preparation containing diltiazem hydrochloride (yield: 0.57 kg).

EXAMPLE 8

The controlled release pharmaceutical preparation (1.12 kg) containing diltiazem hydrochloride obtained in the same manner as in Example 3 was put into CF apparatus and spray-coated with a coating solution consisting of diltiazem hydrochloride (151 g), polyvinylpyrrolidone (12 g), ethanol (87 g) and water (203 g). Then the preparation was dried at 60° C. for 16 hours to obtain a controlled release pharmaceutical preparation containing diltiazem hydrochloride, wherein the part which rapidly released diltiazem hydrochloride was provided in its surface layer.

EXAMPLE 9

To diltiazem chloride (4.8 kg) was added a solution of polyvinylpyrrolidone (K30) (0.15 kg) dissolved in water (0.3 kg). The mixture was kneaded, dried at 45° C. for 4 hours and granulated by sieving with 32 mesh sieve. To the obtained granule (4.5 kg) was added magnesium stearate (45 g) and the mixed powder thereof was tabletted to give plain tablets containing diltiazem hydrochloride, which have the diameter of 5 mm and the weight of 50 mg per tablet.

Then plain tablets (4.0 kg) were put into the coating apparatus (Hi-coater, made by Freund Industrial Co. Ltd., Japan) and spray-coated with a solution consisting of Eudragit RS (224 g), calcium stearate (74 g), triethyl citrate (22 g), ethanol (420 g) and water (860 g). Then the tablets were dried by heating at 60° C. for 16 hours to obtain controlled release tablets containing diltiazem hydrochloride (yield: 4.3 kg).

EXAMPLE 10

Nonpareil 103 which was a spherically granulated sucrose having the diameter of 350 to 500 μm (1500 g) was put into CF apparatus and rolled in it. Thereto was gradually spread fine powder of nicotinamide (NA) (900 g) with spraying a solution of sucrose (135 g) in a mixture (465 g) of ethanol and water (1:3). The plain granule having the diameter of 12 to 20 mesh (1400 to 840 μm) containing NA, wherein Nonpareil was coated around its surface with NA, was thus prepared.

Then the obtained plain granule (0.5 kg) containing NA was put into CF apparatus and spray-coated with a solution consisiting of Eudragit RS (105 g), calcium stearate (35 g), triethyl citrate (11 g), ethanol (200 g) and water (400 g). Then the granule was dried by heating at 60° C. for 16 hours to obtain a controlled release pharmaceutical preparation containing NA (yield: 0.56 kg).

EXAMPLE 11

The procedure was carried out in the same manner as in Example 10 except that phenylpropanolamine hydrochloride was used instead of NA to obtain a controlled release pharmaceutical preparation containing phenylpropanolamine hydrochloride (yield: 0.56 kg).

EXAMPLE 12

The procedure was carried out in the same manner as in Example 10 except that bisoprolol fumarate was used instead of NA to obtain a controlled release pharmaceutical preparation containing bisoprolol fumarate (yield: 0.56 kg).

EXAMPLE 13

The procedure was carried out in the same manner as in Example 10 except that ascorbic acid was used instead of NA to obtain a controlled release pharmaceutical preparation containing ascorbic acid (yield: 0.56 kg).

EXAMPLE 14

The procedure was carried out in the same manner as in Example 10 except that thiamine hydrochloride was used instead of NA to obtain a controlled release pharmaceutical preparation containing thiamine hydrochloride (yield: 0.56 kg).

EXAMPLE 15

The procedure was carried out in the same manner as in Example 10 except that pyridoxine hydrochloride was used instead of NA to obtain a controlled release pharmaceutical preparation containing pyridoxine hydrochloride (yield: 0.56 kg).

EXAMPLE 16

Nonpareil 103 which was a spherically granulated sucrose having the diameter of 500 to 710 μm (1.04 kg) was put into CF apparatus and rolled in it. Thereto was gradually spread a mixed powder of fine powder of (+)-(2S,3S)-3-acetoxy-8-chloro-5-[2-(dimethylamino)ethyl]-2,3-dihydro-2-(4-methoxyphenyl)-1,5-benzothiazepin-4(5H)-one. maleate (hereinafter referred to as Clentiazem) (1.176 kg) and succinic acid (1.96 kg) with spraying a solution of sucrose (0.78 kg) in the mixture of ethanol and water (1:3) (2.22 kg). The plain granule having the diameter of 12 to 24 mesh (1400 to 710 μm) containing Clentiazem, wherein Nonpareil was coated around its surface with Clentiazem, was thus prepared.

Then the obtained plain granule (1 kg) containing Clentiazem was put into CF apparatus and spray-coated with a solution consisiting of Eudragit RS (279 g), calcium stearate (93 g), triethyl citrate (28 g), ethanol (533 g) and water (1067 g). After coating, the granule was dried by heating at 60° C. for 16 hours to obtain a controlled release pharmaceutical preparation containing Clentiazem (yield: 1.38 kg).

In addition to the ingredients used in the Examples, other ingredients can be used in the Examples as set forth in the specification to obtain substantially the same results.

What we claim is:

1. A controlled release pharmaceutical preparation comprising
   (a) a core containing a medicinal compound and
   (b) a coating layer on the surface of the core, said coating layer containing
      (i) a water-repellant salt selected from the group consisting of calcium stearate and magnesium stearate and
      (ii) a water-insoluble and slightly water-permeable copolymer of ethyl acrylate, methyl methacrylate and @-acryloyloxyethyltrimethylammonium chloride,
   the ratio of the water-insoluble and slightly water-permeable copolymer to the water-repellent salt being from 0.5:1 to 5:1 by weight.

2. The pharmaceutical preparation of claim 1, wherein the ratio of the water-insoluble and slightly water-permeable copolymer to the water-repellent salt is from 1.5:1 to 4.5:1 by weight.

3. The pharmaceutical preparation of claim 1, wherein the ratio of the water-insoluble and slightly water-permeable copolymer to the water-repellent salt is from 2:1 to 4:1 by weight.

4. The pharmaceutical preparation of claim 1, wherein another coating layer made of at least one material selected from the group consisting of ethylcellulose, hydroxypropylcellulose and a medicinal compound is provided around the coating layer on the surface of the core.

* * * * *